United States Patent [19]
Faircloth

[11] Patent Number: 5,955,682
[45] Date of Patent: Sep. 21, 1999

[54] PORTABLE SENSOR MANIFOLD FOR AIR CONDITIONING DIAGNOSTICS

[75] Inventor: John E. Faircloth, Jacksonville, Fla.

[73] Assignee: Federal Air Conditioning Technologies, Inc., Calexico, Calif.

[21] Appl. No.: 08/969,070

[22] Filed: Nov. 12, 1997

[51] Int. Cl.[6] .................................................. G01N 1/00
[52] U.S. Cl. ....................................................... 73/863.51
[58] Field of Search ........................... 73/863.33, 863.41, 73/863.43, 863.45, 863.51–863.58, 863.61, 865.5

[56] References Cited

U.S. PATENT DOCUMENTS

| | | | |
|---|---|---|---|
| 3,625,065 | 12/1971 | Thompson | 73/863.51 |
| 3,803,921 | 4/1974 | Dieterich | 73/863.51 |
| 4,615,224 | 10/1986 | Smith et al. | 73/863.33 |
| 4,653,334 | 3/1987 | Capone | 73/863.41 |
| 4,860,598 | 8/1989 | Bailey et al. | 73/863.51 |
| 4,946,650 | 8/1990 | Rothele | 73/863.58 |
| 5,096,670 | 3/1992 | Harris et al. . | |
| 5,108,704 | 4/1992 | Bowers et al. . | |
| 5,141,719 | 8/1992 | Fernwood et al. . | |
| 5,625,156 | 4/1997 | Serrels et al. | 73/863.51 |

FOREIGN PATENT DOCUMENTS

| | | | |
|---|---|---|---|
| 3803352 | 8/1989 | Germany | 73/863.56 |
| 866438 | 9/1981 | U.S.S.R. | 73/863.51 |

*Primary Examiner*—Robert Raevis
*Attorney, Agent, or Firm*—Nydegger & Associates

[57] ABSTRACT

An air sampling system includes a chamber that is formed with an exhaust port and a plurality of intake ports. A plurality of air collector arms are each attached in fluid communication with a respective intake port of the chamber. Further, each collector arm is formed with an inlet slot and an air channel which establishes fluid communications between the inlet slot and the respective chamber intake port. All of the collector arms extend outwardly from the chamber so that their respective inlet slots lie in a first plane. Relative to the inlet slots, the exhaust port of the chamber lies in a second plane that is substantially parallel to the first plane. Accordingly, a portion of the air that passes through the first plane toward the second plane, enters the inlet slots of the collector arms and is diverted into the chamber. In the chamber the diverted air is redirected out the exhaust port. A sensor mounted on the chamber at the exhaust port measures selected characteristics of the diverted and redirected air at the second plane to sample the air that is flowing through the first plane.

10 Claims, 2 Drawing Sheets

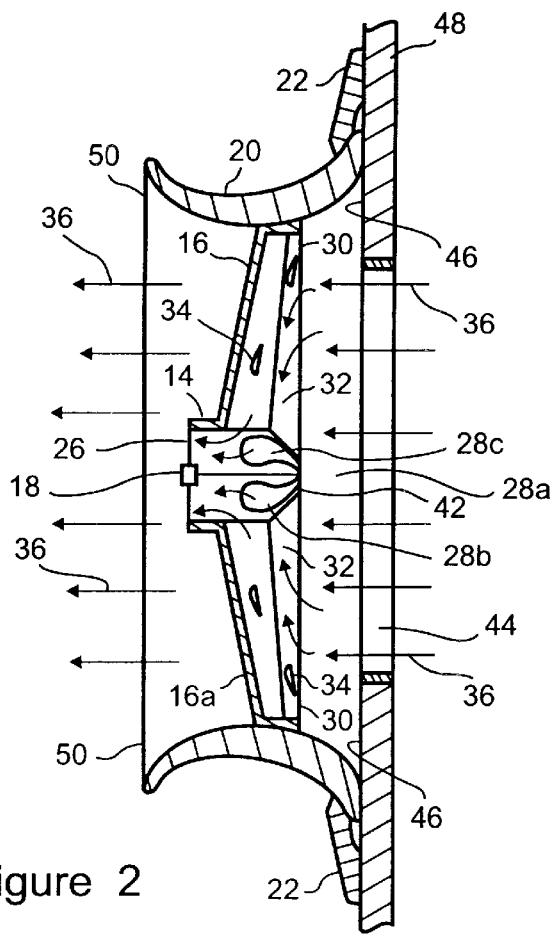
Figure 2
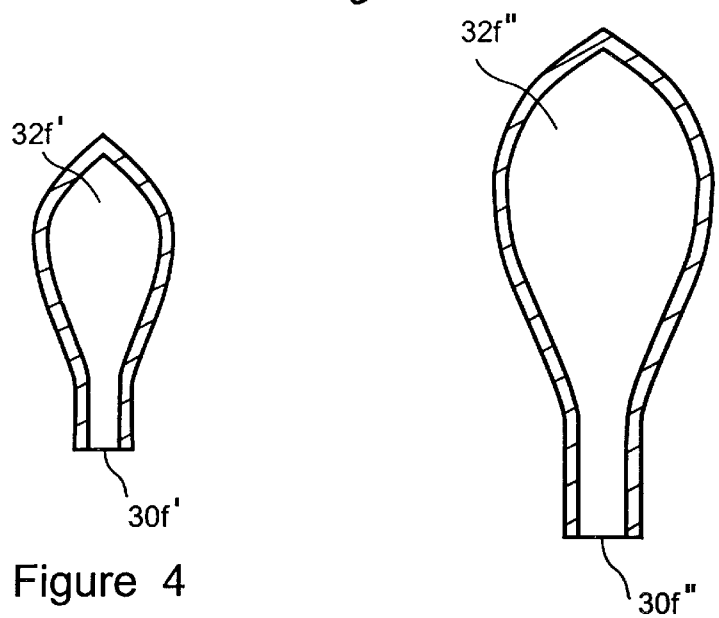
Figure 4
Figure 5

PORTABLE SENSOR MANIFOLD FOR AIR CONDITIONING DIAGNOSTICS

FIELD OF THE INVENTION

The present invention pertains generally to air sampling equipment. More particularly, the present invention pertains to portable air sampling equipment which includes sensors for measuring selected flow characteristics of a volume of air. The present invention is particularly, but not exclusively, useful as a portable diagnostic test system for determining air flow characteristics in an air conditioning system.

BACKGROUND OF THE INVENTION

There are, of course, many reasons why the physical characteristics of a particular volume of air might be of interest. For instance, knowing the temperature, humidity and air flow parameters of a volume of air can be very helpful in determining the effect the air may have on a specific environment. Aside from weather observations, where massive volumes of air must be considered important, there are also many instances when rather small volumes of air need to be analyzed. Specifically, consider air conditioning systems.

Most air conditioning systems rely on the circulation of air through a cycle wherein air from the particular environment to be controlled is passed through equipment that cools the air and returns it to the environment. Whether the particular air conditioning equipment is efficient for accomplishing this task is a matter of some concern. For instance, power efficiency is of interest, as well as is the ability of the equipment to comply with its control inputs.

In the past, in order to determine whether air conditioning equipment was efficient for its intended purposes it was typically necessary to compare the equipment's actual operating characteristics with the operational specifications that are established for the equipment by the manufacturer. Often times, this required invasive measurements of the system coolant. More recently, it has been recognized that the efficiency of an air conditioning system can be noninvasively determined by merely analyzing characteristics of the air that passes through the equipment. For example in U.S. application Ser. No. 08/914,475 which was filed on Aug. 19, 1997 for an invention entitled "DIAGNOSTIC UNIT FOR AN AIR CONDITIONING SYSTEM", and which is assigned to the same assignee as the present invention, noninvasive equipment for diagnosing the efficiency of an air conditioning system has been disclosed.

All systems for diagnosing air conditioning equipment must rely on either measurements of the equipment's operating parameters, measurements of the air that is being conditioned by the equipment, or a combination of the two. When direct measurements of the air are taken, it is necessary to obtain such measurements from a good representative sample of the air. Otherwise, the measurements will be essentially meaningless. For very small volumes of air, this may be a relatively easy matter. Indeed, for very small volumes of air one sensor unit will normally suffice for taking measurements of temperature, humidity and fluid volumetric flow velocities. When larger volumes of air are involved, however, the situation becomes somewhat more complicated.

In order to measure characteristics in the flow of a volume of air through rather large ducts, such as are common for both commercial and residential air conditioning systems, it may be necessary to take several measurements of the air volume. Typically, this is done at several different locations in the fluid air flow. For example, in order to accurately measure the characteristics of air flowing through a five or six square foot orifice of an air duct, ten or twelve samples of the air may need to be taken at as many different locations in the orifice. Otherwise, meaningful and reliable readings for the total flow of air through the orifice may not be obtainable. Not surprisingly, this can be time consuming and tedious.

In light of the above it is an object of the present invention to provide an air sampling system which is able to simultaneously collect diverse samples from a volume of air and combine them into a single sample that is representative of the entire volume of air as it flows through an orifice. Another object of the present invention is to provide an air sampling system which is able to direct a representative sample of air toward a single sensor for an analysis which determines the average characteristics of the entire volume of air from which the sample is taken. It is yet another object of the present invention to provide a method for measuring selected characteristics of a volumetric air flow which are useful for diagnosing air conditioning equipment. Still another object of the present invention is to provide a system for sampling volumetric air flow, together with its concomitant method of operation, which is relatively easy to manufacture, simple to use, and comparatively cost effective.

SUMMARY OF THE PREFERRED EMBODIMENTS

In accordance with the present invention, an air sampling system includes a manifold which includes a central chamber, an air flow sensor, and a plurality of collector arms. Specifically, the central chamber of the manifold is formed with an exhaust port and it has a plurality of intake ports. Each of the collector arms of the manifold is independently connected in fluid communication with a respective intake port of the chamber. Preferably, the collector arms are co-planar with each other and they radiate outwardly from the chamber in a spoke-like arrangement. Within this combination, the air flow sensor is positioned in the exhaust port of the chamber to measure the volumetric flow characteristics of air that is diverted into the chamber by the collector arms. Along with the manifold, the sampling system of the present invention includes a shroud which encircles both the collector arms and the chamber, to confine and define the flow of air through the sampling system. Additionally, the sampling system may include a flexible skirt which is attached to the shroud. The purpose of the skirt is to help establish a fluid tight seal between the shroud and a wall while the shroud is positioned against the wall to surround an air duct.

In more detail, each of the air collector arms of the sampling system for the present invention is formed with an air channel, and each collector arm has an inlet slot which is in fluid communication with the air channel. Further, the air channel is in fluid communication with a respective intake port of the control chamber. Both the air channel and the inlet slot extend substantially along the entire length of their respective collector arms. As a design feature, the inlet slot is tapered with decreasing width in a direction from its unconnected end toward the end where it connects with an intake port of the chamber. In this same direction, the air channel in the collector arm has an increasing cross sectional area. As an additional design feature, the area for the opening of the collector arm's inlet slot should be substantially the same as the area of the chamber's intake port to which the collector arm is connected. Likewise, the cross sectional area of the central chamber's exhaust port should be substantially the same as the sum of the areas of the chamber's various intake ports.

As contemplated for the present invention, all of the inlet slots on the various collector arms are arranged so as to be substantially co-planar. Thus, the inlet slots may be considered to define or establish a first plane. At the same time, the exhaust port of the chamber may be considered to lie in a second plane which is substantially parallel to the first plane. Within this geometrical arrangement, a volume of air that is to be sampled by the system of the present invention can be directed to pass through the sampling system from the first plane to the second plane in a direction that is substantially perpendicular to the planes.

In its operation, the air sampling system of the present invention is positioned against a wall and over an air duct of an air conditioning system. Specifically, the system is positioned over the duct with the shroud completely surrounding the duct. This also places the skirt in contact with the wall surrounding the duct to confine all of the air flowing through the duct and direct it through the sampling system. Also, this places the plane of the air collector inlet slots (the first plane) substantially perpendicular to the direction of air flowing into or out of the duct. In either case, a portion of the air flowing through the shroud, and thus past the sampling system, will be diverted by the air collector arms from its normal direction of flow. Specifically, the diverted air is moved through the collector arm toward the central chamber of the sampling system. As this air is diverted, it is mixed in the air channels of the respective collector arms. Upon entering the central chamber, the diverted air is redirected toward the air flow sensor where air flow characteristics such as temperature, humidity and velocity are measured. A microprocessor is connected with the sensor to further analyze these characteristics for purposes determined by the operator.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 2 is a cross sectional view of the air sampling system of the present invention as seen along the line 2—2 in FIG. 1, with the air sampling system operationally positioned over an air duct;

FIG. 4 is a cross sectional view of a collector arm of the present invention as seen along the line 4—4 in FIG. 3; and FIG. 5 is a cross sectional view of a collector arm of the present invention as seen along the line 5—5 in FIG. 3.

DESCRIPTION OF THE PREFERRED EMBODIMENT

Figure 1:
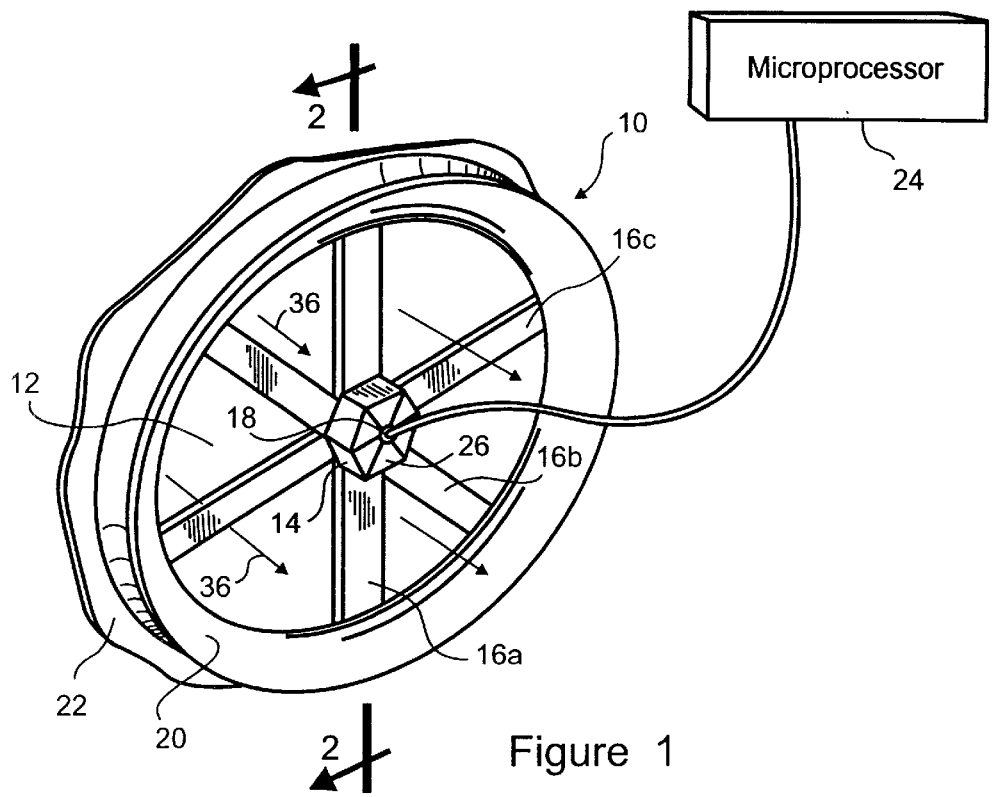
FIG. 1 is a perspective view of the air sampling system of the present invention.

Referring initially to FIG. 1, an air sampling system in accordance with the present invention is shown and generally designated 10. As shown in FIG. 1 the system 10 includes a manifold 12 which comprises a central chamber 14 and a plurality of collector arms 16. The collector arms 16, of which the collector arms 16a 16b and 16c shown in FIG. 1 are exemplary, are attached in fluid communication with the central chamber 14. Additionally, the system 10 includes an air flow sensor 18 which is mounted within the central chamber 14 substantially as shown. Further, a shroud 20 can be used which encircles the manifold 12. Also, a skirt 22 which is attached to the shroud 20 may be included. Finally, the system 10 includes a microprocessor 24 which is connected in signal communication with the sensor 18. By way of example, as will be appreciated by the skilled artisan, the microprocessor 24 may be in hard wire connection with the sensor 18 (as shown), or alternatively, communication between the sensor 18 and the microprocessor 24 can be established by radio frequency transmissions. In either case, the microprocessor 24 is most likely a component part of a larger computer system (not shown) which can be assembled according to well known technologies for the intended purposes of the present invention.

As perhaps best seen in FIG. 2, the central chamber 14 of manifold 12 is formed with an exhaust port 26 and a plurality of intake ports 28, of which the intake ports 28a, 28b and 28c are exemplary. Further, it is to be appreciated that each collector arm 16 is connected or attached to the central chamber 14 for fluid communication with the chamber 14 through a respective intake port 28. With reference back to FIG. 1, it will be seen that the plurality of collector arms 16 radiate or extend from the central chamber 14 in a spoke-like manner. With reference to both FIG. 1 and FIG. 2 it will be seen and appreciated that the plurality of collector arms 16 substantially lie in the same plane. The detailed construction of the collector arms 16, however, will be best appreciated by cross referencing FIG. 2 and FIG. 3.

Figure 3:
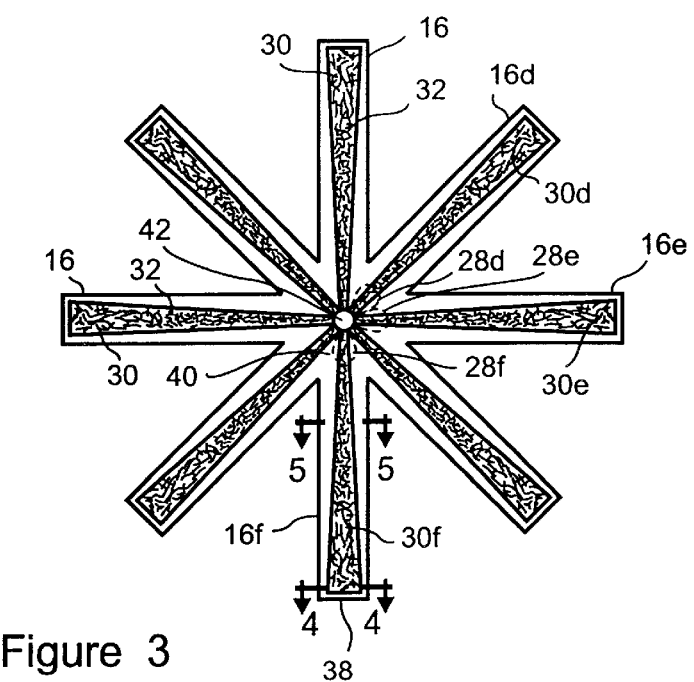
FIG. 3 is a plan view of the sampling system of the present invention as seen when looking at the plane of the collector arm inlet slots, with the inlet slots shaded for clarity.

Although the manifold 12 shown in FIG. 3 has eight collector arms 16, rather than six as shown in FIG. 1, in all other respects the manifolds 16 are the same.

In FIG. 3 it is seen that each collector arm 16 is formed with an inlet slot 30 which extends substantially along the entire length of the respective collector arm 16. In FIG. 2 it is also seen that the inlet slots 30 allow for fluid movement into air channels 32 which are formed in each of the collector arms 16. Also in FIG. 2, it can be seen that the air channels 32 may include several vanes 34 which are mounted in the air channels 32 to mix fluid (air) as it passes through the particular air channel 32. As intended for the present invention, air flow through the system 10 (as represented by the arrows 36) will pass through the shroud 20. A portion of this air flow 36 will be diverted by the manifold 12 and used as a sample of the entire air flow. Specifically, as best seen in FIG. 2, the air to be sampled enters through the inlet slots 30 of the collector arms 16. After this air enters through the slots 30 it is diverted through the air channel 32 where it is mixed by the vanes 34 before entering the central chamber 14 through the intake port 28. In the chamber 14 the air to be sampled is redirected out of the manifold 12 and through the exhaust port 26. As this air exits through the exhaust port 26 it is moving in its original direction of movement and is measured by the sensor 18. Signals carrying these measurements are sent to the microprocessor 24 for further analysis.

The dimensional relationships between cross sectional areas of different components in the system 10 are important, and need to be appropriately engineered. This is so in order for the sample air volume that is collected for measurement to be truly representative In overview, the intent of the present invention is to collect, as a representative sample, a certain percentage of the total air flow volume passing through a plane. Measure this sample, and then discharge this sample back into the air volume as the same percentage of the total air flow volume. To do this, certain dimensions are critical. Most specifically, the system 10 dimensions of importance include the inlet slots 30 of the collector arms 16, the intake ports of the central chamber 14 and the exhaust port 26 of the central chamber 14.

In FIG. 3 it is seen that the inlet slot 30 of collector arm 16f is tapered with a generally diminishing width in the direction from end 38 toward end 40. This fact is further illustrated in FIGS. 4 and 5 where it is comparatively shown that the width of inlet slot 30f' at end 38 (FIG. 4) is larger than the width of inlet slot 30f" closer to the end 40 (FIG. 5). The intent here is that the percentage of the total air flow which passes through inlet slot 30 into the manifold 12 should generally constant, regardless of the length of the collector arm 16. Thus, the width of inlet slot 30 will be generally proportional to the distance from the hub 42 of manifold 12. Stated differently, most air is collected at end 38, with proportionately less air being collected at points progressively closer to the end 40 at hub 42. At the same time, by comparing FIGS. 3, 4 and 5, it will be noted that the cross sectional area of air channel 32 increases as the width of inlet slot 30 decreases. This is necessary in order to accommodate the larger volume of air that is diverted from the collector arms 16 toward the central chamber 14. Thus, the air channel 32f' at end 38 is smaller than air channel 32f' closer to end 40.

As a general proposition, the cross sectional area of an intake port 28 will be about the same as the cross sectional area of the inlet slot 30 which feeds air into the intake port 28. Thus, in FIG. 3, the total cross sectional area of the inlet slot 30f will be substantially equal the total cross sectional area of the intake port 28f (shown in phantom in FIG. 3). Similarly, for example, the inlet slots 30d,e of collector arms 16d,e will have cross sectional areas that are substantially equal to the respective cross sectional areas of the intake ports 28d,e (also shown in phantom in FIG. 3).

It is also to be appreciated that the sum of the cross sectional areas of all intake ports 28 for central chamber 14 is substantially equal to the total cross sectional area of exhaust port 26. Thus, the volume of air which enters the inlet slots 30 of the collector arms 16 will return to the main stream of air at substantially the same velocity. On the other hand, due to the mixing actions of the vanes 34 and the collector arms 16, the temperature and relative humidity of the volume of returned air will be representative of the total air volume that passes through the shroud 20.

In the operation of the system 10, it is to be understood that the system 10 is effective for collecting air samples from supply ducts as well as return ducts. In FIG. 2 the system 10 is shown sampling a return duct 44, wherein air flows from the duct 44 toward the system 10 (note the direction of the arrows 36). As shown, for this arrangement, the edge 46 of shroud 20 is positioned against the wall 48. On the other hand, in order to sample a supply duct 44, wherein air flows through the system 10 before entering the duct 44 (i.e. reverse the directions of arrows 36) the system 10 is merely turned so that the edge 50 of shroud 20 positioned against the wall 48.

While the particular Portable Sensor Manifold for Air Conditioning Diagnostics as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. An air sampling system which comprises:
    a chamber formed with an exhaust port and at least one intake port;
    at least one air collector arm formed with an air channel and an inlet slot, said collector arm being attached to said chamber and extending therefrom to establish fluid communication through said air channel between said inlet slot of said collector arm and said intake port of said chamber; and
    a sensor mounted with said chamber and positioned in said exhaust port to measure temperature, volumetric flow and relative humidity of air flowing from said inlet slot to said exhaust port.

2. A system as recited in claim 1 wherein said inlet slot defines a first area and said exhaust port defines a second area, and wherein said first area is substantially equal to said second area.

3. A system as recited in claim 2 wherein said first area lies in a first plane and said second area lies in a second plane, and wherein said first plane is substantially parallel to said second plane.

4. A system as recited in claim 3 wherein said collector arm has a first end and a second end, with said first end being attached in fluid communication to said intake port of said chamber, and said second end being extended a distance from said chamber in said first plane, and wherein said inlet slot is tapered to decrease from said second end toward said first end.

5. A system as recited in claim 4 further comprising a shroud for interconnecting said second end of said collector arm to direct airflow toward and through said first plane.

6. A system as recited in claim 5 further comprising a skirt attached to said shroud for sealing said system to define an air flow to be sampled by said sensor.

7. A system as recited in claim 1 wherein said inlet slot of said collector arm defines an area and said intake port of said sampling chamber defines an area, and wherein said area of said inlet slot is substantially equal to said area of said intake port.

8. A method for determining selected characteristics of a volume of air passing sequentially through a first plane and a second plane, wherein the first plane is substantially parallel to the second plane and the air volume travels in a direction substantially perpendicular to the first and second planes, the method which comprises the steps of:
    diverting the movement of a portion of the air volume at the first plane into a direction substantially parallel to the first plane;
    redirecting the diverted portion of the air volume toward the second plane in a direction of travel substantially perpendicular to the second plane;
    measuring characteristics of the diverted air at the second plane, said measured characteristics being temperature, volumetric flow and relative humidity; and
    using the measured characteristics of the diverted air as being representative of the selected characteristics of the volume of air.

9. A method as recited in claim 8 further comprising the step of mixing the diverted portion of the air volume.

10. A method as recited in claim 8 wherein said diverting step is accomplished by using a scoop positioned in said first plane and said redirecting step is accomplished by using a chamber attached in fluid communication with said scoop.

* * * * *